United States Patent [19]

Ongley

[11] 4,252,019

[45] * Feb. 24, 1981

[54] SAMPLE MIXER AND SPLITTER FOR CONTINUOUS FLOW CENTRIFUGATION SAMPLING

[76] Inventor: Edwin D. Ongley, R.R. 3, Bath, Ontario, Canada, K0H 1G0

[*] Notice: The portion of the term of this patent subsequent to Feb. 24, 1998, has been disclaimed.

[21] Appl. No.: 52,953

[22] Filed: Jun. 28, 1979

[51] Int. Cl.³ .................................................. G01N 1/18
[52] U.S. Cl. ................................................... 73/421 A
[58] Field of Search ............. 73/421 R, 421 A, 421 B, 73/422 R

[56] References Cited

U.S. PATENT DOCUMENTS

| | | | |
|---|---|---|---|
| 2,742,788 | 4/1956 | Henton | 73/422 R |
| 3,120,128 | 2/1964 | Snyder | 73/421 B |

OTHER PUBLICATIONS

Houser, E. A., Principles of Sample Handling and Sampling Design for Process Analysis, Instrument Society of America, Pittsburgh, Pa., 1972, pp. 9, 10 & 32.

*Primary Examiner*—S. Clement Swisher

*Attorney, Agent, or Firm*—Richard J. Hicks; Stanley E. Johnson

[57] ABSTRACT

A method and apparatus for the quantitative recovery of solids suspended in a fluid from such fluid involving continuous flow centrifugation. Samples of the fluid with the particles suspended therein, are simultaneously pumped from a plurality of source locations into a common chamber wherein they become mixed while being continuously fed thereto. The samples from the mixing chamber flow to a sample splitting chamber from which a portion is diverted to a continuous flow centrifuge and the remaining diverted to waste. The quantity of mixed sample fed to the centrifuge is determined so that the quantity of solids collected in the centrifuge can be related thereto. The apparatus includes a plurality of pump units, each having a water inlet and a water outlet, a sample mixer consisting of a chamber having inlets thereto for receiving the water samples from the pump units. The sample mixer communicates directly with a sample splitting chamber having a first outlet open to atmosphere and a second outlet downstream thereof which is connected to the inlet of a continuous flow centrifuge.

12 Claims, 5 Drawing Figures

SAMPLE MIXER AND SPLITTER FOR CONTINUOUS FLOW CENTRIFUGATION SAMPLING

This invention is related to the following applications filed concurrently herewith:

(a) U.S. Pat. Application Ser. No. 52,957 filed June 28, 1979 entitled "Continuous Flow Centrifugation Method of Sampling"

(b) U.S. Pat. Application Ser. No. 52,956 filed June 28, 1979 entitled "Continuous Flow Centrifugation Sampling Apparatus"

This invention relates to a method and apparatus for sampling, and more particularly, a continuous flow system for quantitative recovery, by continuous-flow centrifugation, of solids suspended in a fluid. The invention particularly is directed to a method and apparatus for quantitative recovery of suspended solids from a flowing body of water, such as a river, and will be described herein with reference to such. It is to be understood, however, the method and apparatus is applicable to quantitative recovery of suspended solids from any fluid.

The term "quantitative" refers to the ability of the invention to collect suspended solids from a fluid medium in a manner which:

1. is consistent with the state-of-art of conventional suspended solids monitoring techniques as practiced by government agencies such as the United States Geological Survey and the Sediment Survey of Canada;

2. collects suspended solids in such a manner that the collected sample accurately reflects:

gravimetric characterization of solids per unit volume of sampled medium.

representative fractions of organic and/or mineral suspended matter in the sampled medium.

particle size distribution of solids within the sampled medium.

chemical characteristics of solids and fluid of the sampled medium.

3. permits calculation of error terms associated with any of the items under #2 above, which accrue due to site factors, inefficiencies inherent to continuous-flow centrifugation, and potential chemical contamination by materials from which the invention may be constructed.

To assess the impact of point and non-point pollutant sources upon river and lake water quality it is necessary to assess the roll of suspended solids in the fluvial transport of significant quantities of nutrient and contaminants. This assessment involves annual, seasonal, inter or intra-storm variation of physical and chemical properties of suspended solids.

The conventional practice of water sampling involves collection of small volumes of water, usually less than one liter, on which a limited range of physical and chemical tests can be performed. Testing for a wide variety of chemical characteristics now known to be associated with suspended solids (e.g. trace metals, many pesticides—especially organochlorine residues, phosphorus, radio nucleides) and for corelative physical information (e.g. particle size distributions, mineralogy, organic/inorganic components) requires a substantial quantity of suspended matter which can not be acquired by conventional methods of small volume sampling, nor conveniently by large volume sampling together with filtration, bench centrifugation or flocculation. These latter large volume techniques require the physical transport of large volumes of water to a laboratory and produce inaccurate results due to settling and chemical change during elapsed time between sampling and processing. Such techniques do not lend themselves to routine monitoring operations.

An alternative technology involving continuous-flow centrifugation has been tested to a very limited extent in the past. This has involved either the use of a pump (or pumps) and a valve with which to control the rate of flow into the centrifuge, or one or more containers in which the sampled water is stored and thence pumped slowly at a controlled rate of flow into a centrifuge. In the first case, the control valve does not split the sample, thereby causing a pressurized system in which the rate of flow between the submersible pump and centrifuge is slowed down to that point where settling and chemical change can occur in the connecting hose. In the second case, pumped samples are often trucked considerable distances to a centralized processing site. Whether or not transport of samples occurs, settling and chemical change occurs during the storage of the sampled water. Moreover, the very large volume of water which must be stored requires the provision of large containers thereby adding substantially to the logistics base required for such an operation.

In the aforementioned continuous-flow centrifugation tests, little or no care was directed to the attitude of the pump or pumps in the water column and were placed on the river bottom. Pump units placed on the river bottom or in the water column without regard to pump attitude with respect to stream velocity or flow direction produce samples which are not representative of the sampled medium.

A principal object of the present invention is to provide an improved method and apparatus for quantitative sampling which overcomes the drawbacks of the conventional practice.

This object is met by the present invention which broadly comprises a continuous flow system that will be described in more detail hereinafter. The invention involves a method of sampling, an apparatus for carrying out the sampling method as well as specific components of the apparatus and various combinations thereof.

In accordance with a first aspect of the present invention there is provided a method for the quantitative recovery of solids suspended in a fluid from such fluid comprising pumping samples of the fluid, with the particles suspended therein, from two or more different source locations and into a common chamber, mixing the samples in said chamber as they are continuously fed thereinto, causing said mixed samples to flow into a sample splitter, causing a portion of the mixed samples to flow from the sample splitter into a continuous-flow centrifuge, and diverting the remaining portion of the mixed samples to waste, the amount of mixed samples fed to the centrifuge being determined so that the quantity of solids collected in the centrifuge can be related thereto.

Applicant's particular method comprises pumping samples of water from different source locations in a flowing stream by pumps where the rate of flow into the pumps is preferably at the same rate as the flow rate of the stream. Mixing in the chamber is effected by pumping at such rate, relative to the size of the chamber, as to cause turbulent flow therein.

In accordance with a second aspect of the present invention there is provided an apparatus for carrying out the foregoing method which comprises a plurality of pump units each having a water inlet and a water outlet, a sample mixing chamber having inlets thereto connected to the outlets of the pump units, a sample splitter communicating with the mixing chamber and having a first outlet therefrom to waste and a second outlet therefrom communicating with an inlet to a centrifuge, the flow to the latter being at a determined controlled rate. The sample splitter is preferably a vertical, elongate chamber with the first outlet being an open port in a side wall thereof and the second outlet at a lower elevation with flow through the latter being controlled by a flow control valve.

In accordance with a third aspect of the present invention there is provided in combination a sample mixer, a sample splitter and a continuous flow centrifuge, said sample mixer comprising a first chamber for receiving and mixing a plurality of samples therein from different source locations, said sample splitter comprising a second chamber communicating with said first chamber and having a first outlet discharging to waste and a second outlet discharging directly to an inlet of the continuous flow centrifuge.

In accordance with a fourth aspect of the present invention there is provided a sample mixer and splitter unit for use in a continuous flow water sampling apparatus comprising: a first elongate sample mixing chamber having a plurality of inlets thereto at positions spaced apart from one another longitudinally therealong, a second elongate sample splitting chamber communicating with said first chamber, a first outlet from said second chamber located adjacent an end thereof remote from the first chamber and a second outlet from said second chamber, said second outlet being at a position between said first chamber and said first outlet.

The present application is directed to the above mentioned third and fourth aspects of the invention and U.S. Pat. application Ser. Nos. 52,957; 52,956 are directed to respective first and second aspects of the invention.

The invention is illustrated by way of example with reference to the accompanying drawings, wherein.

Figure 1:
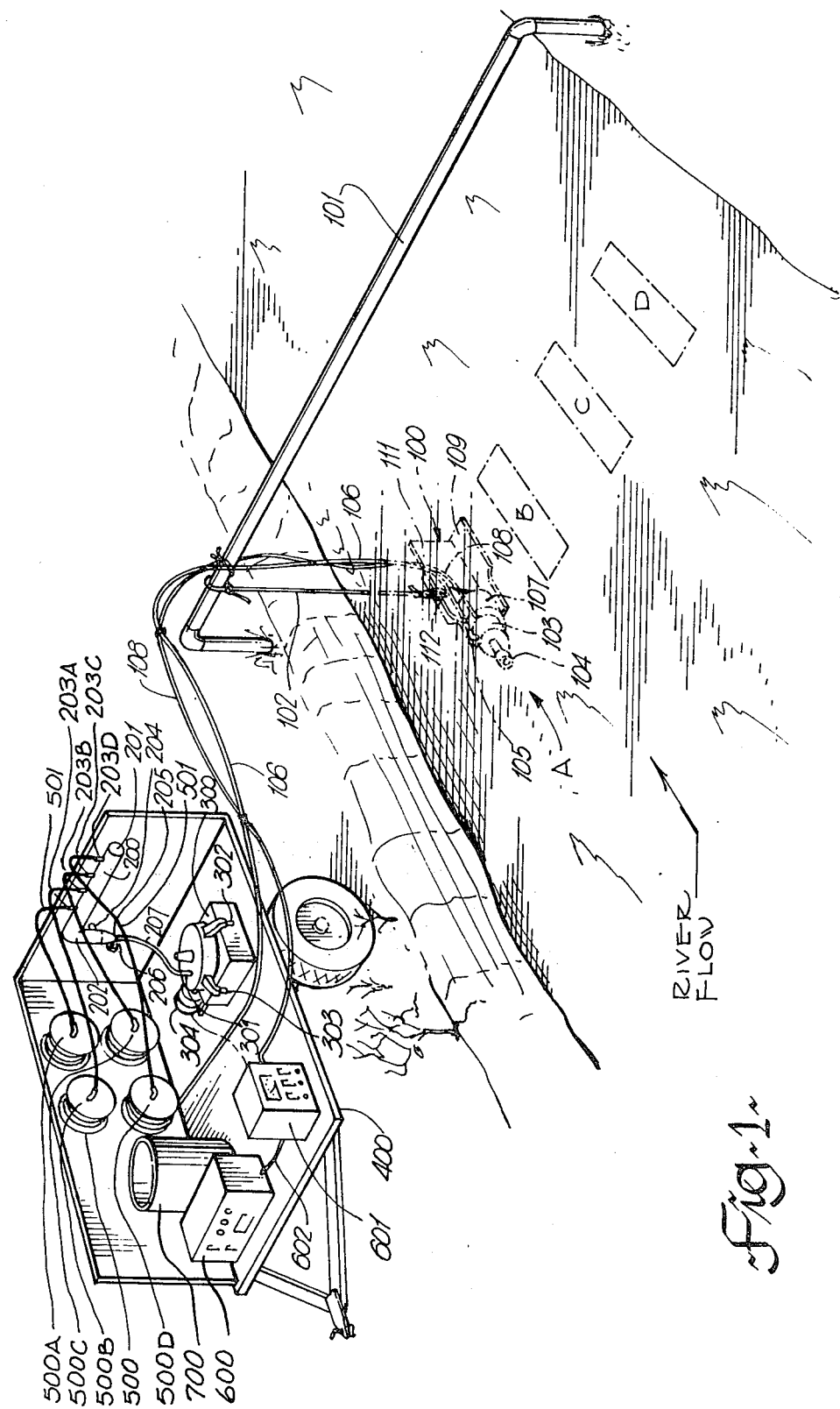
FIG. 1 is an oblique diagrammatic view illustrating the overall system of sampling provided in accordance with the present invention.
Figure 2:
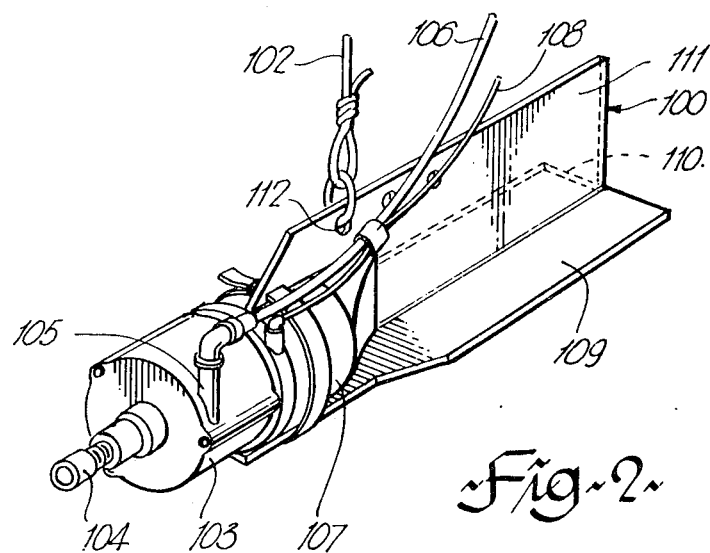
FIG. 2 is an enlarged view of one of the submersible pump units.

Referring to the drawings, there is illustrated a field portable sampling apparatus for collecting samples from a flowing stream and passing such samples through a centrifuge to remove solid particles suspended in the water. The system is a continuous flow system in that the samples are pumped directly from the river through a sample mixer to a sample splitter and flow from the latter to a continuous-flow centrifuge. The samples are pumped from different source locations into a first chamber portion where they are mixed. The mixed samples flow to a second chamber portion (a sample splitter) from which a portion of the samples are directed into a continuous-flow centrifuge and the remainder discharged to waste.

The mixed samples are in actual fact directed to an unpressurized aqueous sample splitter which turbulently maintains all particulates in suspension whilst directing a portion of the mixed samples to a continuous-flow centrifuge and the remaining amount to waste.

The basic components of the apparatus are a plurality of submersible pumps 100, a sample mixer and splitter 200 and a continuous flow centrifuge 300. The pumps 100 are suspended from an overhead support 101 (for example, a bridge crossing a river) by cables 102 submersing the pumps a select distance below the surface of the water and above the river bed. The pumps are located at four different sample source locations designated A, B, C and D, transversely across the flowing stream.

Each pump unit consists of a pump 103 having an inlet 104 and an outlet 105. The inlet 104 is a nozzle threaded onto a spigot projecting forwardly of the pump so that the inlet may be readily changed to different sizes. In sampling, it is preferable that the flow of water through the intake 104 be at the same rate as the river stream flow. The inlet size can readily be determined when the pumping rate has been determined. The outlet is curved rearwardly and attached to a flexible hose 106. The curved outlet, which is a rigid elbow, serves as a connector for connecting the hose 106 to the pump outlet and appropriately directs the hose so that the flowing stream will not cause the hose to crimp. The pump is driven by an electric motor 107 having a power supply cord 108 attached thereto. The combined pump and motor unit is mounted on an orientation controlling apparatus consisting of a pair of horizontal fins 109 and 110 and a vertical fin 111. The vertical fin 111 is a steering fin which, by virtue of the flowing water, causes the inlet 104 of the pump to be directed directly into the stream flow. The horizontal fins 109 and 110 maintain appropriate horizontal orientation so as to direct the inlet 104 of the pump directly into the stream. The cable 102 is attached to the vertical fin at a position designated 112 so that the entire assembly is in horizontal balance when suspended from the cable.

The sample mixer and splitter 200 and the centrifuge 300 are mounted on a trailer unit 400 providing portability for the entire apparatus. On the trailer there are four hose reels 500, one being provided for each of the submersible pump units. The flexible hose 106 of the respective pump units at source locations A, B, C and D is wound onto respective ones of the reels 500A, 500B, 500C and 500D.

The sample mixer and splitter 200 consists of a horizontal mixing chamber 201 communicating directly with a vertically downwardly depending sampler splitter chamber 202. The mixing chamber 201 has four inlets thereto; i.e., one for each of the pumps, such inlets being designated 203A, 203B, 203C and 203D. The reel 500A has a flexible hose 501 therefrom communicating with the flexible hose 106 through suitable piping in the reel and such hose 501 is connected to mixer inlet 203A. Similarly, hoses from the pumps at source locations B, C and D are connected to inlets 203B, 203C and 203D.

From the foregoing it will be readily apparent water is pumped from locations, A, B, C and D by pumps 100 at respective source locations A, B, C and D by way of the flexible hoses to respective ones of the inlets 203A, 203B, 203C and 203D of the mixing chamber 201. The vertically disposed sample splitter chamber 202 has respective first and second outlets 204 and 205. The outlet 204, in a side wall of the sample splitter, discharges to waste and the outlet 205 is in the bottom of the sample splitter chamber. A flow control valve 206 regulates the amount of the mixed samples fed to the inlet 301 of the continuous flow centrifuge 300, outlet 205 being connected to inlet 301 by a flexible hose 207. The centrifuge 300 is a stock item and one found in practice suitable for this purpose is an Alfa-Laval MAB 102 industrial clarifier. The centrifuge has respective outlets 302 and 303.

Mounted on the trailer 400 is a portable power source 600, for example, a 1500 kw gasoline engine driven generator. Power from this unit is fed to a control box 601 by way of a cable 602 from which control box power to the motor 604 of the centrifuge and the pump units can be individually controlled. Also carried on the trailer 400 is a water barrel or drum 700 for collecting, should one desire, a bulk sample to be later analyzed in a laboratory for comparative results.

The water sampling procedure consists of transporting the equipment (mounted on a trailer or in a truck) to a flowing stream and placing the pumps approximately mid-depth at different positions across the stream. The stream flow rate is measured before submersing the pumps and a suitable nozzle selected and placed on the pump.

The pump inlet 104 consists of interchangeable nozzles of differing inside dimensions so that, knowing the current velocity at the chosen sampling depth and the pumping rate at the particular head, a nozzle can be chosen which permits an intake velocity which matches the stream velocity and which does not reduce the rate of flow through the connecting hose. Fine tuning of this arrangement can be accomplished if desired by a valve located between the pump and the mixing chamber.

Figure 3:
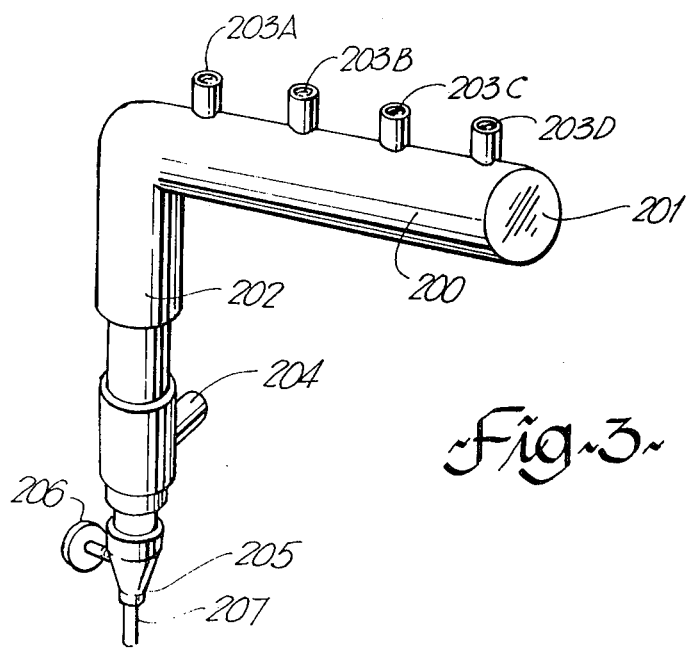
FIG. 3 is an enlarged view of a sample mixer and splitter for the system illustrated in FIG. 1.

The flow rate into the sample splitter, during sampling, is equal to the free outflow therefrom. The splitter is thus unpressurized. The discharge to waste from the splitter is through an open port located at a higher elevation than the outlet from the sample splitter to the centrifuge. Good field results having been obtained using a combined mixer and splitter as shown in FIG. 3 and positioning it so that chamber 201 is horizontal and chamber 202 depending vertically downwardly therefrom.

The following is an example of a water sampling test and results obtained in actual use of an apparatus constructed in accordance with the present invention. In such apparatus the size of inlet 104 = 1.0 cm I.D. (0.394")
the size of hoses 106 (connected directly to mixer inlets) = 1.59 cm I.E. (0.625")
internal diameter of chamber 201 = 3.81 cm I.D. (1.5")
internal diameter of chamber 202 = 3.81 cm I.D. (1.5")
length of chamber 201 = 65 cm (25.6")
length of chamber 202 = 32 cm (12.6")
size and spacing of inlets 203A, 203B, 203C, 203D = $\frac{3}{4}$" NPS (female) 13.5 cm (5.3") apart (centre to centre)
internal diameter of hose 207 = 1.3 cm (0.5")
internal diameter of outlet 204 = 3.0 cm (1.2")

In the test the equipment was set up adjacent a bridge and the pumps suspended from the bridge railing. The stream velocity was determined to be approximately 3.6 m/sec (generally determined by current meter located at pump depth). Three submersible pump units (Little Giant #4-SMD units) were located at mid-depth at positions $\frac{1}{4}$, $\frac{1}{2}$, and $\frac{3}{4}$ distance across the stream. Pump intake nozzles selected were 1.0 cm I.D. (at a processing head of 15 ft., a 1.0 cm nozzle allows a good match between stream velocity and pump intake velocity for the pump, hose combination used). Each pump was connected to mixing chamber 201 by 125 ft. $\frac{5}{8}$" I.D. rubber hose. The centrifuge was an Alfa-Laval MAB102 and the flow thereto at a rate of 6 liters/min. The rate of flow through the centrifuge can be readily determined by a timed volumetric measurement on the outlet (discharge) side of the centrifuge and is adjusted by valve 206 of FIG. 3.

Bulk Recovery Efficiency for test $$100 - \frac{\text{Output (from centrifuge) solids concentration}}{\text{Input (to centrifuge) solids concentration}} = 85.\%$$

Field and laboratory experiments confirm that recovery efficiency is dependent upon rate of flow through centrifuge, organic/mineral ratio, particle size distribution. An improvement in recovery efficiency occurred when processing at 4 liters/min. in a later test.

Volume pumped through centrifuge: 810 liters
Pumping time: 135 minutes
Set-up and take-down time: approximately 15 minutes each.
Personnel requirements: 1 person Note: Nozzle dimension can be selected by using the equation of continuity:

| Discharge = Area (of nozzle cross-section) × Current velocity |
|---|
| (cm³/sec)    (cm²)    (cm/sec) |

Where "discharge per pump" is measured at the mixing chamber, and "current velocity" is measured by current meter at pump depth.

Test Results

Physical Characteristics of Recovered Solids
60.33 g. solids recovered
6.39% is organic (by loss on ignition)
93.61% is mineral sediment
Sub-sieve (dispersed) particle-size distribution of mineral sediment (by Sedigraph 5000D) as %. (u is microns)

| | | |
|---|---|---|
| 62–31u = 10% | 31–16u = 11% | 16–8u = 09% |
| 8–4u = 7% | 4–2u = 11% | 2–1u = 12% |
| 1–.5u = 10 | .5–.2u = 8% | <.2u = 22% |

Chemical Characteristics of Recovering Solids
Total Trace Metals (ppm of freeze-dried sediment) by A.A.

| (atomic absorption spectrophotometry) |
|---|
| Ni=25  Cu=26  Zn=128  Pb=21  Co=10  Mn=625  Cd=<0.4 |

DPTA Extractable Trace Metals (ppm) by A.A.

| Ni = 0.8  Cu = 5.5  Zn – 14.8  Pb = 5.2  Co = 0.4  Mn = 83. |
|---|

Phosphorus Forms (ppm) by CCIW (Canada Centre Inland Waters) method as elemental P

| | |
|---|---|
| Apatite-P = 491 | Nonapatite Inorganic-P = 317 |
| Organic-P = 430 | Total Inorganic-P = 820 |
| Total-P = 1250 | |

Major Elements (ppm) by X-Ray Fluorescence

| Fe2O3 | =5.36 | TiO2 | = 0.86 | CaO | = 7.18 | K2O | =3.26 |
|---|---|---|---|---|---|---|---|
| MnO | = .08 | SiO2 | =61.94 | Al2O3 | =13.55 | MgO | =3.38 |
| P2O5 | =0.34 | NaO2 | = 2.44 | | | | |

Figure 5:
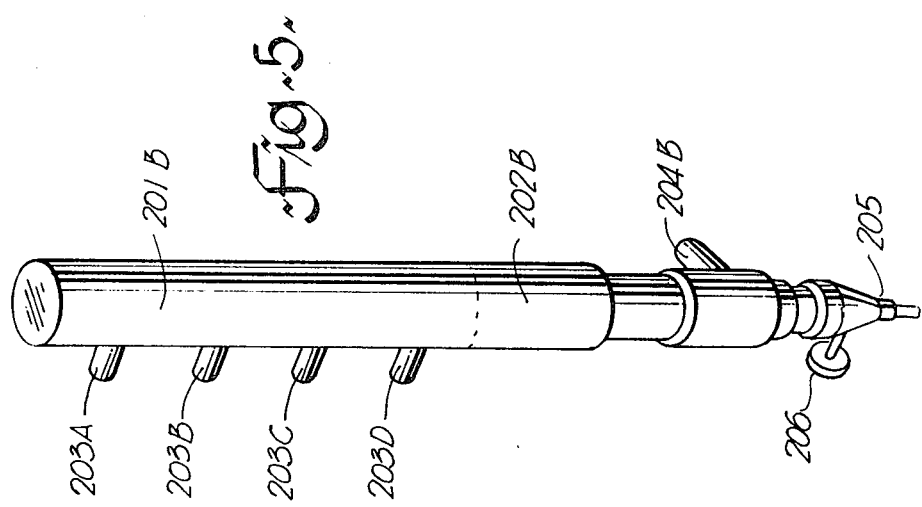
FIG. 5 illustrates a still further modified sample mixing and splitter chamber.

In the foregoing described apparatus the mixing chamber and the sample splitting chamber are a single unit and angularly disposed with respect to one another, the mixing chamber being horizontal and the splitting chamber vertical. An alternative is illustrated in FIG. 5 wherein the two chambers are vertical and disposed in end to end axial alignment. If desired they could be laterally offset from one another. Referring to FIG. 5 there is a mixing chamber 201B having a plurality of inlets thereto designated 203A, 203B, 203C and 203D. The inlets are illustrated vertically one above the other at different vertical locations, but if desired they may be variously positioned. For example, they can be at different peripheral locations, and at the same vertical location. The function of the mixing chamber in all embodiments is to maintain the flow turbulent so that the suspended particles are carried with the flow of water and do not separate or settle out therefrom. The sampling splitting chamber 202B is vertically below the sampling mixing chamber and has an overflow outlet 204B therefrom for diverting to waste selected quantities of water. Flow from the bottom end of the splitting chamber is controlled by way of a ball valve 206 through a hose 207 to a continuous flow centrifuge. The chambers 210B and 202B are contiguous with one another and are provided by a longitudinal length of pipe closed at the top and having the flow control ball valve 206 at the lower end thereof.

Figure 4:
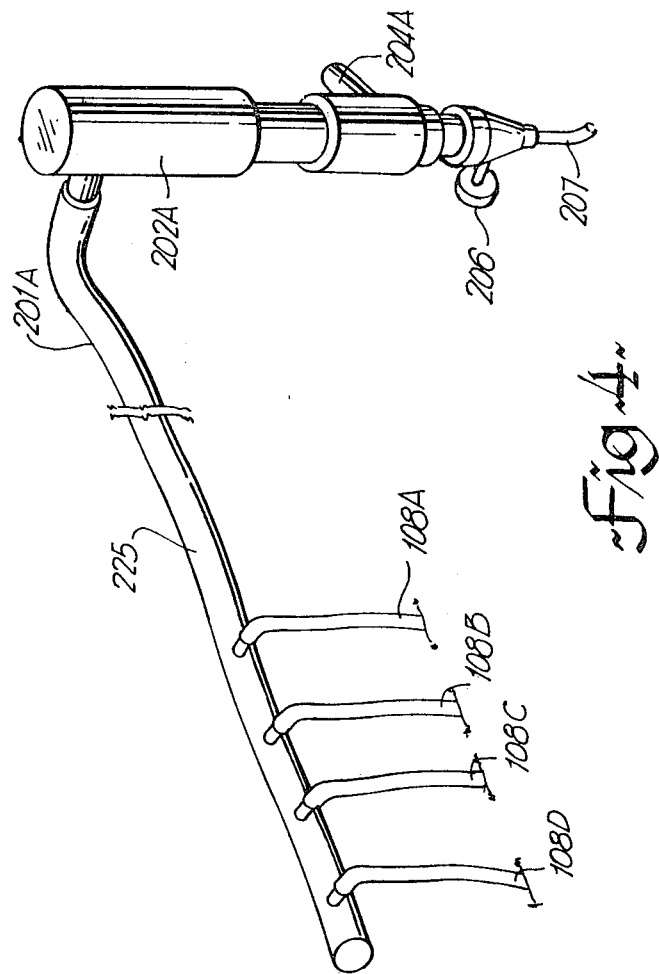
FIG. 4 illustrates as an alternative, separate mixing and splitter chambers.

In the foregoing embodiments, the mixing chamber and the sample splitting chamber are a single unit. Alternatively, however, they may be separate and FIG. 4 illustrates such an embodiment. In this embodiment the mixing chamber consists of a length of hose 225 having the pump hoses 108A, 108B, 108C and 108D connected thereto adjacent one end thereof, for example, at the bridge railing or support 101. The other end of the hose 225 is connected to the splitter chamber 202A which is mounted on the trailer. The entire hose 225 may be flexible or alternatively a combination of rigid pipe and flexible hose. The splitter chamber 202A is provided by a vertically disposed rigid length of pipe closed at the top end and having a first over-flow outlet 204A in a side wall thereof and a second outlet connected to the centrifuge 300 by a hose 207 through flow control ball valve 206.

All embodiments are a continuous flow system and the sample splitter is operated in a non-pressurized state. To accomplish this the over-flow is a free flow through the waste or outlet aperture 204.

In the foregoing the pumps have been described and illustrated as being submersible and having orientation controlling means thereon. It is possible, should one desire, to locate the pumps on land and have the inlets thereto submersed in the stream in which case the inlets are mounted on orientation means ensuring the inlets are directed into the flow of the stream. By means of buoyancy means and/or suspension means the inlet can be maintained at an appropriate depth in the stream for sampling and which is normally mid-depth of the stream. It may sometimes be necessary to add additional weight to the pumps (or submersed inlets) to ensure their stability in a fast flowing stream and ensure they remain submersed.

I claim:

1. For use in sampling suspended solids in a fluid medium, the combination of a sample mixer, a sample splitter and a continuous flow centrifuge; said sampler mixer having a first chamber therein for receiving and turbulently mixing a plurality of samples of a fluid medium containing suspended solids from different source locations, and said sample splitter for splitting said turbulently mixed samples into a first and second position comprising a second chamber communicating with said first chamber, and having a first outlet for discharging said first portion to waste and a second outlet, connected to an inlet of the continuous flow centrifuge, through which said second portion passes for quantitative recovery of said suspended solids in said continuous flow centrifuge.

2. The combination of claim 1 wherein said chambers are elongate, cylindrical chambers connected end-to-end.

3. The combination of claim 2 wherein said chambers are angularly disposed with respect to one another.

4. The combination of claim 3 wherein said chambers are at right angles to one another.

5. The combination of claim 2 wherein said chambers are disposed in vertical end-to-end alignment, said sample splitter chamber being at the lower elevation of the two chambers.

6. The combination of claim 4 wherein said second outlet is at an end of the second chamber remote from said first chamber.

7. The combination of claim 6 including an adjustable flow control valve in said second outlet.

8. The combination of claim 1 including a plurality of inlets to said first chamber.

9. A sample mixer and splitter for use in a continuous flow sampling system for sampling suspended solids in a fluid medium, comprising first and second elongate chambers communicating with one another and disposed in angular relation with respect to each other for turbulently mixing samples therein, a plurality of inlets to said first chamber for receiving water samples containing suspended solids from a plurality of different source locations, a first overflow outlet from said second chamber for directing a first portion of mixed samples to waste and a second outlet from said second chamber downstream from said first outlet for directing a second portion of mixed samples to a continuous flow centrifuge.

10. A sample mixer and splitter as defined in claim 9 wherein said first and second chambers are in contiguous relation.

11. A sample mixer and splitter as defined in claim 10 wherein said chambers are at right angles to one another.

12. A sample mixer and splitter as defined in claim 9 wherein said inlets are spaced apart from one another longitudinally along said first chamber.

* * * * *

UNITED STATES PATENT AND TRADEMARK OFFICE
CERTIFICATE OF CORRECTION

PATENT NO. : 4,252,019
DATED : February 24, 1981
INVENTOR(S) : Edwin D. Ongley

It is certified that error appears in the above-identified patent and that said Letters Patent are hereby corrected as shown below:

On the cover page the Notice should read:

--The portion of the term of this patent subsequent to Feb. 17, 1998, has been disclaimed.--

Column 2, line 28 should read --the pump or pumps in the water column or were--.

Column 5, line 48 "I.E." should read --I.D.--.

Column 6, line 12, the equation should read:

$$100 - \frac{100 \times \text{Output (from centrifuge) solids concentration}}{\text{Input (to centrifuge) solids concentration}} = 85.\%$$

Column 6, line 48 "1 - .5u = 10" should read --1 - .5u = 10%--.

Column 6, line 59 "Zn - 14.8" should read --Zn = 14.8--.

Column 7, line 32 "210B and 202B" should read --201B and 202B--.

Column 8, line 14 (Claim 1) should read --bulently mixed samples into first and second portions--.

Signed and Sealed this

Twenty-eighth Day of July 1981

[SEAL]

Attest:

GERALD J. MOSSINGHOFF

Attesting Officer       Commissioner of Patents and Trademarks